(12) United States Patent
Paggel et al.

(10) Patent No.: US 9,170,229 B2
(45) Date of Patent: Oct. 27, 2015

(54) METHOD FOR DIAGNOSING AN ELECTRICAL CONTACT CONNECTION OF AN EXHAUST GAS SENSOR

(71) Applicant: CONTINENTAL AUTOMOTIVE GMBH, Hannover (DE)

(72) Inventors: Jens Paggel, Abensberg (DE); Sirko Schlegel, Neutraubling (DE)

(73) Assignee: Continental Automotive GmbH, Hannover (DE)

( * ) Notice: Subject to any disclaimer, the term of this patent is extended or adjusted under 35 U.S.C. 154(b) by 336 days.

(21) Appl. No.: 13/775,666

(22) Filed: Feb. 25, 2013

(65) Prior Publication Data

US 2013/0219984 A1  Aug. 29, 2013

(30) Foreign Application Priority Data

Feb. 24, 2012  (DE) .................. 10 2012 202 847

(51) Int. Cl.
| | |
|---|---|
| G01N 27/417 | (2006.01) |
| G01N 27/416 | (2006.01) |
| G01R 31/28 | (2006.01) |
| F02D 41/14 | (2006.01) |
| G01R 31/02 | (2006.01) |
| F02D 41/22 | (2006.01) |
| G01R 31/00 | (2006.01) |

(52) U.S. Cl.
CPC ........ G01N 27/4175 (2013.01); F02D 41/1456 (2013.01); F02D 41/1495 (2013.01); F02D 41/222 (2013.01); G01N 27/4163 (2013.01); G01R 31/026 (2013.01); G01R 31/2832 (2013.01); G01R 31/006 (2013.01); Y02T 10/40 (2013.01)

(58) Field of Classification Search
CPC ............ G01N 27/407; G01N 27/4163; G01N 27/4175
See application file for complete search history.

(56) References Cited

U.S. PATENT DOCUMENTS

2012/0266647 A1   10/2012   Barnikow et al.

FOREIGN PATENT DOCUMENTS

| DE | 102008001697 A1 | 11/2009 |
| DE | 102009050221 A1 | 5/2011 |
| DE | 102010000663 A1 | 7/2011 |

*Primary Examiner* — Paul West
(74) *Attorney, Agent, or Firm* — Laurence A. Greenberg; Werner H. Stemer; Ralph E. Locher

(57) ABSTRACT

A method diagnoses an electrical contact connection of an exhaust gas sensor, in which two current sources are used to impress currents into a pump cell and a reference cell of the exhaust gas sensor. If a line is faulty, the relevant current cannot flow and a voltage on the relevant current source assumes a high value. If a second line is faulty, measurement of the voltage on the second connection, which is connected to the connecting point between the two cells, provides a low value when the relevant second connection is isolated from the reference-ground potential by a second switch, since the cell capacitances have not been able to charge to the reference-ground potential.

3 Claims, 4 Drawing Sheets

METHOD FOR DIAGNOSING AN ELECTRICAL CONTACT CONNECTION OF AN EXHAUST GAS SENSOR

CROSS-REFERENCE TO RELATED APPLICATION

This application claims the priority, under 35 U.S.C. §119, of German application DE 10 2012 202 847.1, filed Feb. 24, 2012; the prior application is herewith incorporated by reference in its entirety.

BACKGROUND OF THE INVENTION

Field of the Invention

The invention relates to a method for diagnosing an electrical contact connection of an exhaust gas sensor having two cells, in which a first of the cells is connected up between a first and a second connection of the exhaust gas sensor and a second of the cells is connected up between the second and a third connection.

The exhaust gas sensors used for exhaust gas after treatment in internal combustion engines are frequently linear lambda probes. In this case, the first cell is what is known as a pump cell of the lambda probe. The second cell is the reference cell of the lambda probe. The common connection of the pump and reference cells is normally connected to a reference-ground potential which has a voltage value of approximately half the supply voltage and may be connected up as a virtual reference-ground potential.

Legal regulations require the exhaust gas sensor to have its electrical contact connection checked. By way of example, if a line for a chip that controls the exhaust gas sensor, what is known as a control ASIC (application specific integrated circuit), has a line fracture or if there is a line fracture within the exhaust gas sensor, an associated malfunction in the lambda control can result in drastic impairment of the exhaust gas behavior of the internal combustion engine.

In contemporary exhaust gas sensors, the diagnosis for checking the electrical contact connection is based on a plausibility check. In order to be able to carry out the plausibility check, it is necessary for the internal combustion engine to have a minimum rotation speed. The identification of a fault in the electrical contact connection, which is also known as open line identification, can also take several minutes, depending on the driving condition, which will no longer be accepted in future by legal guidelines. Similarly, it is not possible to perform the diagnosis for the electrical contact connection during an engine start, i.e. before the internal combustion engine has reached its minimum rotation speed required for operation.

Published, non-prosecuted German patent application DE 10 2008 001 697 A1 discloses an evaluation and control unit for a wideband lambda probe, in which two current sources can be used to impress currents onto the connections of the probe and to measure voltages between the connections. This is intended to allow line fractures to be identified. However, this document does not reveal specifically how this is intended to be accomplished.

SUMMARY OF THE INVENTION

It is accordingly an object of the invention to provide a method for diagnosing an electrical contact connection of an exhaust gas sensor which overcome the above-mentioned disadvantages of the prior art methods of this general type, which easily allows safe identification of a line fracture for an exhaust gas probe.

The invention provides a method for diagnosing an electrical contact connection of an exhaust gas sensor having two cells, in which a first of the cells is connected up between a first and a second connection of the exhaust gas sensor and a second of the cells is connected up between the second and a third connection. The method uses an apparatus containing a first current source, which is connected to the first connection via a first controllable switching element and to the second connection via a second controllable switching element and which can drive a current through the first cell via the first and second connections. A second current source is provided, which is connected to the third connection via a third controllable switching element and to the second connection via the second controllable switching element and which can drive a current through the second cell via the second and third connections. A first voltage measuring device is provided, which is connected up between the first and second connections. A second voltage measuring device is connected up between the second and third connections. A third voltage measuring device is connected up between the second connection and ground potential. The connecting point between the two current sources is connected to a reference-ground potential which has a voltage value of approximately half the supply voltage value, in which: when the switching elements are closed and the first and second current sources are activated, the first voltage measuring device is used to ascertain a first voltage and the second voltage measuring device is used to ascertain a second voltage. A voltage value for the first voltage that is far above the voltage on the first cell on the basis of a current from the first current source, and a voltage value for the second voltage that corresponds to the voltage on the second cell on the basis of a current from the second current source, prompt inference of a contact connection error on the first connection. Wherein a voltage value for the second voltage that is far above the voltage on the second cell on the basis of a current from the second current source, and a voltage value for the first voltage that corresponds to the voltage on the first cell on the basis of a current from the first current source, prompt inference of a contact connection error on the third connection. A voltage value for the first voltage that is far above the voltage on the first cell on the basis of a current from the first current source, and a voltage value for the second voltage that is far above the voltage on the second cell on the basis of a current from the second current source, prompt inference of a contact connection error on the first and third connections or on the second connection. In the last case the second switching element is opened and a third voltage, ascertained by the third voltage measuring device, that is below an adjustable threshold value prompts inference of a contact connection error on the second connection.

The invention has the advantage that the electrical contact connection can be verified both within the starting sequence of an internal combustion engine, i.e. the engine start, and, if required, during the operation of the internal combustion engine. In this case, the electrical contact connection is understood to mean the condition of the wiring harness in terms of an open connection within the wiring harness or within the exhaust gas sensor or within a controller that controls the exhaust gas sensor (e.g. on a printed circuit board). In this case, a wiring harness contains the wires provided between the exhaust gas sensor and the apparatus. The diagnosis design allows the line diagnosis, when needed, with just a brief interruption in the operation of the exhaust gas sensor in the course of operation. The apparatus can be implemented using only a few parts. This means that it can be implemented easily and inexpensively.

If the contact connection is intact, the internal resistance of a cell experiences a voltage drop that is conditional upon the current from the associated current source but that is relatively small on account of the small measurement current. If there is a line interruption, however, then no current can flow and the current source carries the maximum voltage that can be produced by the (real) current source, the voltage being significantly higher than the voltage that can be measured across the internal resistance of a cell for a rated current from the current source. This makes it a simple matter to distinguish a line interruption from an intact contact connection.

On the basis of their design, the cells have a capacitive impedance and are furthermore connected to the appliance ground by parasitic capacitances. They therefore charge to the reference-ground potential when the second switching element is closed and the second connection has an intact contact connection, however, this charging being able to be detected on the second connection over a long time after the second switching element is opened. If the contact connection on the second connection is interrupted, however, this charging of the cell impedances cannot take place, which means that when the second switching element has been opened the second connection is no longer connected to the reference-ground potential and therefore the voltage measured on the second connection by the third voltage measuring device becomes significantly lower, as a result of which the line interruption can be detected on the second connection.

One advantage of the inventive apparatus for diagnosing the electrical contact connection is that the apparatus may be of discrete design. Optionally, it may also be integrated in a microcontroller which interacts with a controller for the exhaust gas sensor, or directly in a controller (control ASIC) for the exhaust gas sensor.

Other features which are considered as characteristic for the invention are set forth in the appended claims.

Although the invention is illustrated and described herein as embodied in a method for diagnosing an electrical contact connection of an exhaust gas sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
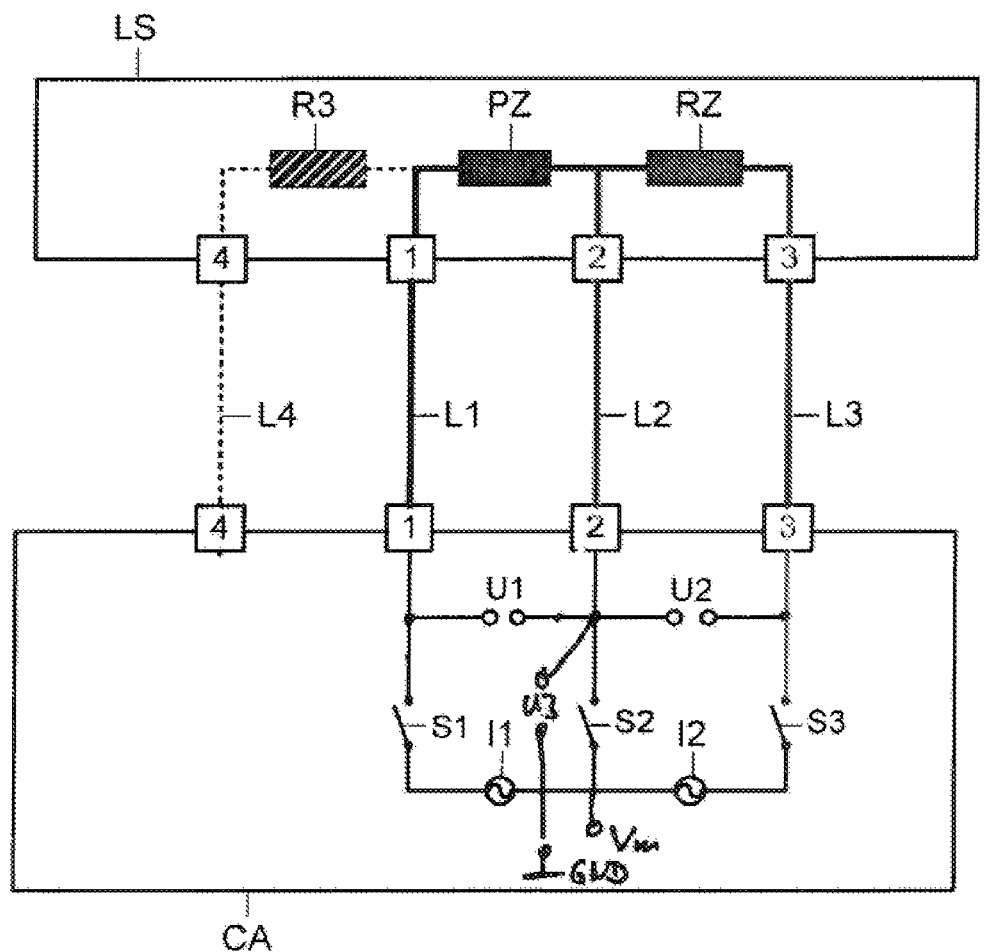
FIG. 1 is a schematic illustration of an apparatus for diagnosing an electrical contact connection of an exhaust gas sensor according to the invention.

Referring now to the figures of the drawing in detail and first, particularly, to FIG. 1 thereof, there is shown a schematic illustration of an apparatus CA for carrying out the inventive diagnosis for the electrical contact connection of an exhaust gas sensor LS in the shape of a linear exhaust gas probe.

The exhaust gas sensor LS contains a pump cell PZ as a first cell and a reference cell RZ as a second cell. The pump cell PZ is connected up between a first connection 1 and a second connection 2 of the exhaust gas sensor. The reference cell RZ is connected up between the second connection 2 and a third connection 3 of the exhaust gas sensor LS. These parts are the minimum configuration for a lambda probe. FIG. 1 shows an optional trimming resistor R3 in dashes, the trimming resistor being provided between the first connection 1 and a fourth connection 4. The trimming resistor R3 is used for compensating for manufacturing tolerances in the probe, i.e. in the resistance value of the pump cell PZ.

The apparatus CA, which contains all the parts for diagnosis for the electrical contact connection, is preferably part of a control application specific integrated circuit (ASIC) of the exhaust gas sensor. Similarly, the parts described below may be arranged in a separate microcontroller, which is then communicatively coupled to the control ASIC which is fundamentally present. A further alternative—which is likewise not shown in the figures—would be for the parts of the apparatus CA to be provided as discrete parts and for them to be electrically connected to the control ASIC.

All the components which are required for controlling the exhaust gas sensor LS are not included in the illustrations described below, for the sake of simplicity. Only those components which are required for the diagnosis for the electrical contact connection are shown.

The second connection 2 is connected via a second switching element S2, in a known manner, to a reference-ground potential Vm which has approximately half the voltage value of the supply voltage and which may be connected up as a virtual reference-ground potential. The circuitry required for this, which keeps the second connection at 2.5 V, for example, when the second switch S2 is closed, is known to a person skilled in the art from the prior art, as a result of which it is also not shown in the schematic illustration. The circuitry required for this is usually provided in the control ASIC.

The apparatus CA contains a number of connections that corresponds to the number of connections of the exhaust gas sensor LS. Connections corresponding to the connections of the exhaust gas sensor LS are likewise denoted by 1, 2, 3, 4. The corresponding or associated connections of the exhaust gas sensor LS and the apparatus CA are connected to one another by lines L1, L2, L3, L4, which are usually present as a wiring harness. The apparatus CA monitors whether there is a line fracture in one of the lines L1 to L4 or whether there is an open connection within the exhaust gas sensor LS (what is known as open line diagnosis).

The apparatus CA contains a first current source I1, which is connected to the first connection 1 via a first controllable switching element S1. The other connection of the current source I1 is connected to the second connection 2 via a second switching element S2. The current source I1 can drive a current between the first and second connections 1, 2. A second current source I2 is connected to the third connection 3 via a third controllable switching element S3. The other end of the second current source I2 is connected to the second connection 2 via the second switching element S2.

According to one expedient embodiment of the apparatus, the first and/or the second current source is/are a DC source or an AC source. Optionally, the first and second current sources are regulated, particularly for different rated currents. This allows simultaneous diagnosis for the electrical contact connection of various connections and lines in the contact connection.

A first voltage measuring device for recording a voltage U1 is connected up between the first and second connections 1, 2. Correspondingly, a second voltage measuring device for recording a voltage 2 is connected up between the second and third connections 2, 3. A third voltage measuring device is connected up between the second connection 2 and the appliance ground GND. The components required for recording the first and second voltages are not shown explicitly, since the embodiment thereof is known in principle to a person skilled in the art.

In one expedient embodiment, the first and/or the second and/or the third voltage measuring device contain(s) a lock-in amplifier for ascertaining a DC voltage when the current sources are in the form of AC sources.

The apparatus CA also contains a controller which is configured to actuate the controllable switching elements S1 to S3 and also the current sources I1 to I2, and to evaluate the voltage values U1 to U3 ascertained by the voltage measuring devices. The controller is not shown in FIG. 1 and the further drawings for the sake of simplicity.

Figure 2:
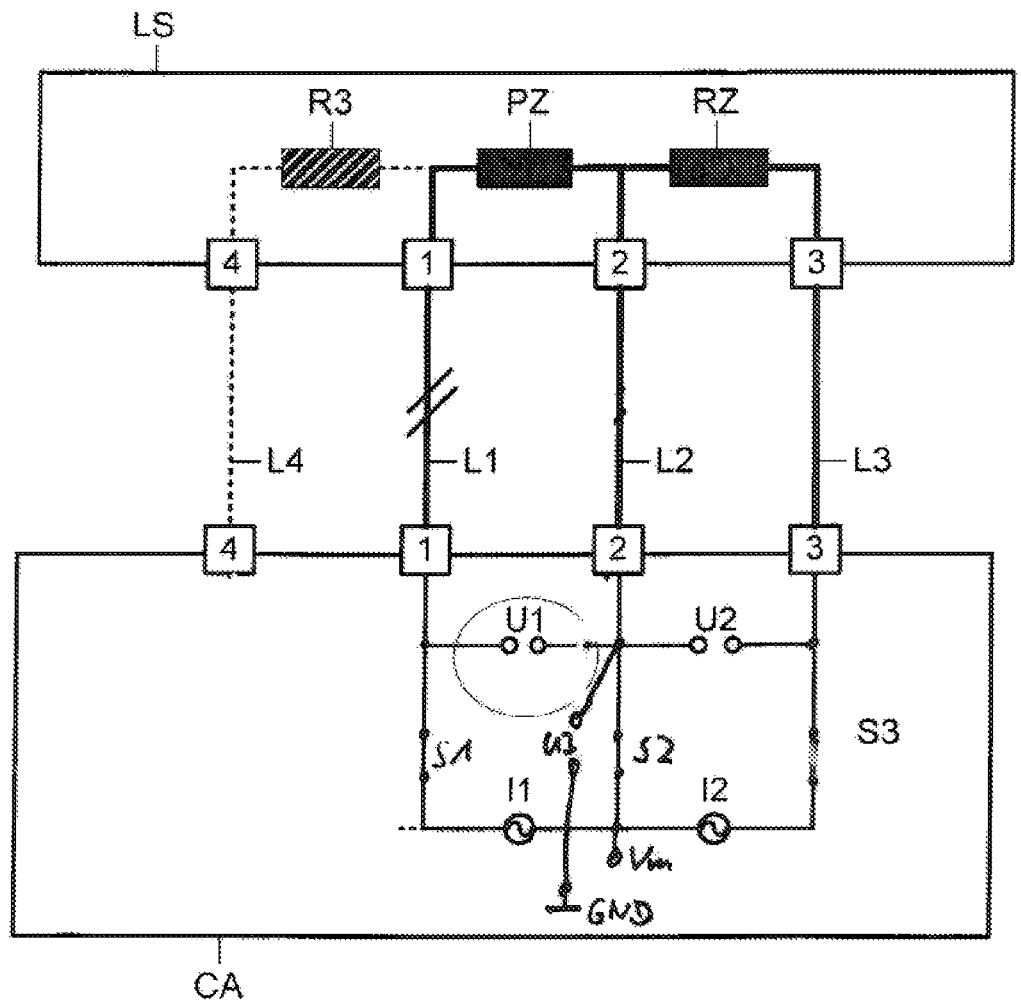
FIG. 2 is a schematic illustration of the arrangement from FIG. 1 during a first measurement step.
Figure 3:
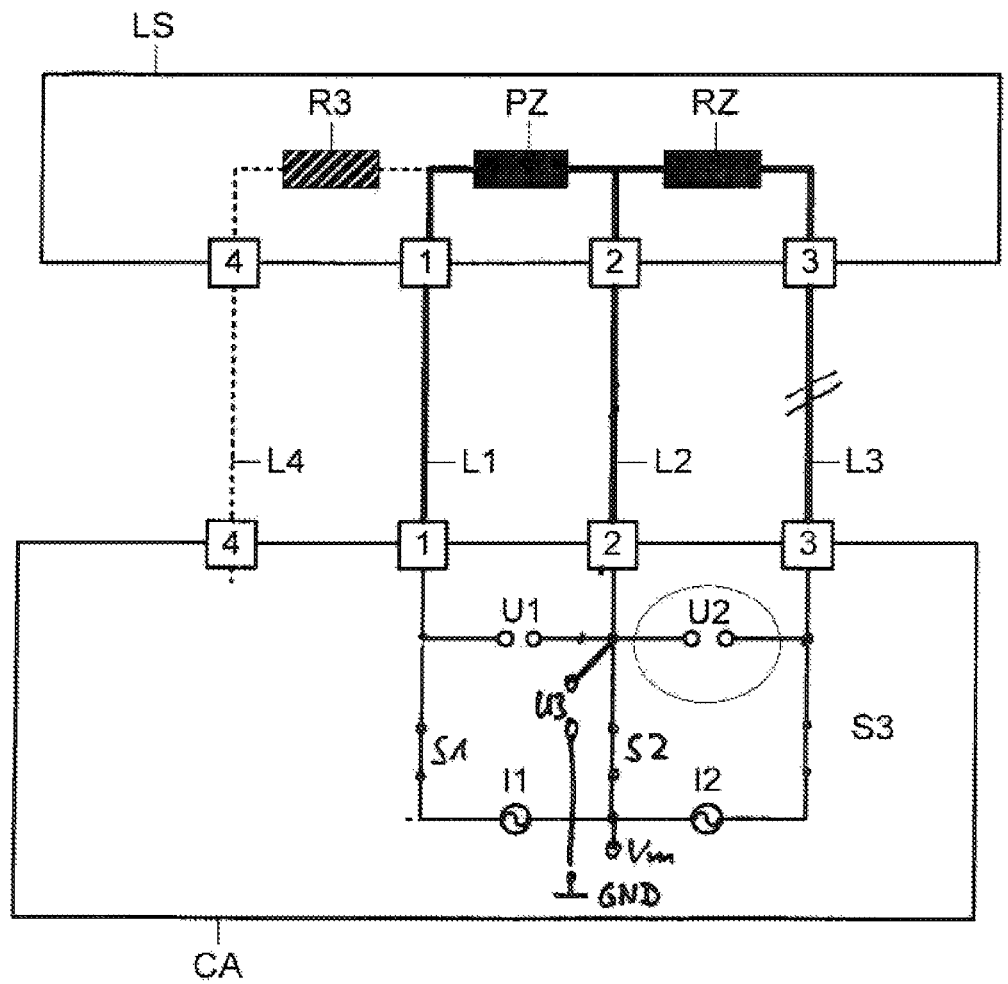
FIG. 3 is a schematic illustration of the arrangement from FIG. 1 during a second measurement step.
Figure 4:
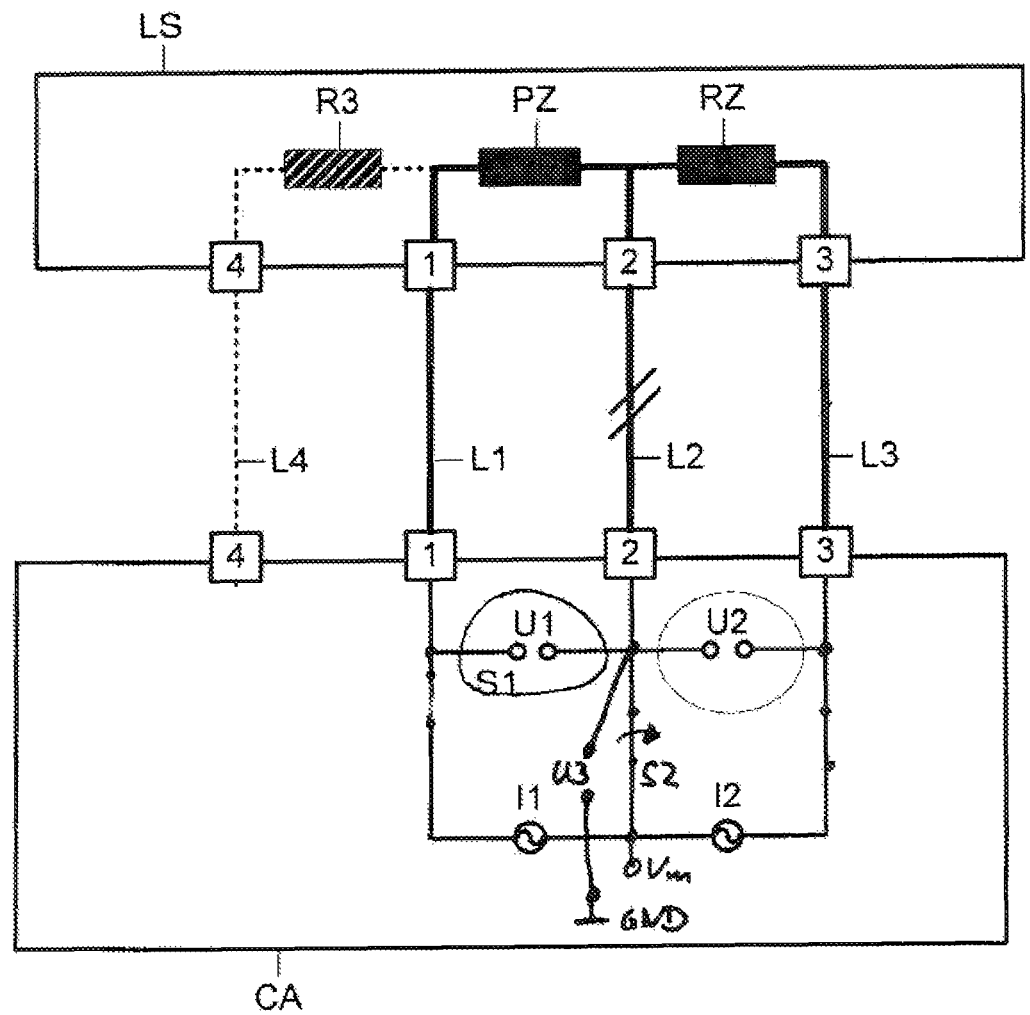
FIG. 4 is a schematic illustration of the arrangement from FIG. 1 during a third measurement step.

The order of the measurement sequence as described by FIGS. 2 to 4 can be implemented in this form. It is likewise possible for the measurement sequence to be carried out in a different order.

In the first measurement sequence shown in FIGS. 2 and 3, all three switching elements S1, S2 and S3 are closed. Furthermore, the first and second current sources I1, I2 are activated and the voltages U1 and U2 are ascertained by the first and second voltage measuring devices. As a result of a current being impressed by the first current source I1 and the second current source I2, intact lines L1 to L3 prompt a respective voltage drop to be produced across the internal resistance of the pump cell PZ and of the pump cell RZ. The internal resistance of the pump cell PZ is usually in the region of 300Ω, and that of the reference cell RZ is usually in the region between 75Ω and 300Ω. If the lines L1, L2 and L3 and also all lines relating to the pump cell PZ and the reference cell RZ are in order, voltages U1 and U2 will appear which result from the currents produced by the current sources I1 and I2 and from the internal resistances of the pump cell PZ and the reference cell RZ. Since the internal resistances and the currents are known, plausible voltage values can be ascertained therefor.

By way of example, approximately square-waveform currents are impressed into the cells PZ, RZ. On account of phase shifts and charging/discharging processes in the exhaust gas sensor LS, approximately triangular-waveform, time-shifted voltages U1, U2 are obtained which have a rather flat profile in the "positive case".

If one the lines L1 or L3 has an interruption, on the other hand, then the line interruption carries the maximum voltage that can be produced by the respective current source I1 or I2. This results in a very much higher voltage U1 or U2, which can be detected easily by a suitable choice of threshold value for the voltage U1 and U2.

Thus, if the voltage U1 is below its threshold value and the voltage U2 is above its threshold value, the line L3 is faulty. Conversely, the line L1 is faulty if the voltage U2 is below its threshold value and the voltage U1 is above its threshold value.

If both voltages U1 and U2 are above their threshold values, either the lines L1 and L3 or the line L2 are/is faulty, since no current can flow.

In this case, there follows a second measurement sequence, which is shown in FIG. 4. The second switching element S2 is opened and the voltage U3 is ascertained. If the latter drops below a prescribed threshold value, the line L2 is faulty, since the capacitances of the probe cells PZ and RZ have not been able to charge to the reference-ground potential Vm and, when the second switching element S2 has been opened, the second connection 2 is no longer connected to the reference-ground potential Vm and therefore the voltage on the second connection 2 falls quickly, since parasitic capacitances quickly discharge via the third voltage measuring device.

If the current sources I1 to I3 are in the form of AC sources, the apparatus can be implemented such that frequency demodulation is automatically performed and the AC voltage brought about by the alternating current is directly available. For this purpose, the voltage measuring devices contain lock-in amplifiers, which are known to a person skilled in the art. This allows the complexity of circuitry to be reduced.

The implementation described for the measurement sequence according to the invention can advantageously be implemented as early as when the engine starts and also continually during operation of the exhaust gas sensor. This requires only a brief interruption in the operation of the exhaust gas measurement.

The invention claimed is:

1. A method for diagnosing an electrical contact connection of an exhaust gas sensor having two cells, a first of the cells is connected up between a first and a second connection of the exhaust gas sensor and a second of the cells is connected up between the second and a third connection, which comprises the steps of:

providing an apparatus containing:
a first current source being connected to the first connection via a first controllable switching element and to the second connection via a second controllable switching element and the first current source can drive a current through the first cell via the first and second connections;
a second current source connected to the third connection via a third controllable switching element and to the second connection via the second controllable switching element and the second current source can drive a current through the second cell via the second and third connections;
a first voltage measuring device connected up between the first and second connections;
a second voltage measuring device connected up between the second and third connections; and
a third voltage measuring device connected up between the second connection and ground potential, a connecting point between the two current sources is connected to a reference-ground potential which has a voltage value of approximately half a supply voltage value;

using the first voltage measuring device to ascertain a first voltage and the second voltage measuring device to ascertain a second voltage when the first, second and third switching elements are closed and the first and second current sources are activated;

prompting an inference of a contact connection error on the first connection if a voltage value for the first voltage is above a voltage on the first cell on a basis of the current from the first current source and a voltage value for the second voltage corresponds to a voltage on the second cell on a basis of the current from the second current source;

prompting an inference of a contact connection error on the third connection if the voltage value for the second voltage is above the voltage on the second cell on a basis of the current from the second current source and the voltage value for the first voltage corresponds to the voltage on the first cell on a basis of the current from the first current source; and prompting an inference of a contact connection error on the first and third connections or on the second connection if the voltage value for the first voltage is above the voltage on the first cell on a basis of the current from the first current source and a voltage value for the second voltage is above the voltage on the second cell on a basis of the current from the second current source, and determining that the contact connection error is on the second connection and not on the first and third connections by opening the second switching element and ascertaining by means of the third voltage measuring device, that a third voltage is below an adjustable threshold value.

2. The method according to claim 1, which further comprises ascertaining the first, second and third voltages during an operation of the exhaust gas sensor.

3. The method according to claim 1, which further comprises ascertaining the first, second and third voltages independently of the operation of an internal combustion engine which contains the exhaust gas sensor.

\* \* \* \* \*